United States Patent [19]
Berceaux

[11] Patent Number: 4,818,228
[45] Date of Patent: Apr. 4, 1989

[54] OCCLUSION SIMULATOR

[76] Inventor: Pierre Berceaux, 39, bd Henri Henrot, F-51100 Reims, France

[21] Appl. No.: 72,258
[22] PCT Filed: Oct. 17, 1986
[86] PCT No.: PCT/FR86/00357
  § 371 Date: Jun. 16, 1987
  § 102(e) Date: Jun. 16, 1987
[87] PCT Pub. No.: °WO87/02234
  PCT Pub. Date: Apr. 23, 1987

[30] Foreign Application Priority Data
  Oct. 18, 1985 [FR]  France .................. 85 15524

[51] Int. Cl.⁴ ............................. A61C 11/00
[52] U.S. Cl. .............................. 433/54; 433/55; 433/57; 433/58
[58] Field of Search .................. 433/54–68; 128/777

[56] References Cited
U.S. PATENT DOCUMENTS

| | | |
|---|---|---|
| 2,119,579 | 6/1938 | Hagman et al. |
| 2,430,525 | 11/1947 | Miller ............... 433/54 |
| 2,621,407 | 12/1952 | Schlesinger . |
| 2,748,481 | 6/1956 | Glueck ............... 433/55 |
| 3,593,424 | 7/1971 | Lee ..................... 433/55 |
| 3,832,777 | 9/1974 | Tinder ................ 433/52 |
| 4,103,424 | 8/1978 | Benjamin et al. ... 433/58 |
| 4,417,873 | 11/1983 | Kulas ................. 433/57 |

FOREIGN PATENT DOCUMENTS

| | | |
|---|---|---|
| 148231 | 9/1952 | Australia ............. 433/54 |
| 814924 | 9/1951 | Fed. Rep. of Germany . |
| 1262504 | 5/1968 | Fed. Rep. of Germany . |
| 788623 | 10/1935 | France . |

Primary Examiner—Larry Jones
Attorney, Agent, or Firm—Cushman, Darby & Cushman

[57] ABSTRACT

This occlusion simulator for dental prostheses, reproducing mandible motions, mainly consists of two articulated forks connected by a small rod. The upper fork is connected to the small rod via the fork-holder and the longitudinal articulation pin. The lower fork is connected to the small rod via the lower fork-holder and the ball-joint whose lateral excursion is limited by side plates mounted on the sides of the upper fork-holder and by pistons with return springs.

13 Claims, 3 Drawing Sheets

OCCLUSION SIMULATOR

BACKGROUND OF THE INVENTION

1. Field of the Invention

This invention concerns an occlusion simulator for dental prostheses reproducing the mandible motions.

2. Prior Art

Presently, prosthodontists use simple hinged occlusion systems, allowing vertical motion, in some cases supplemented by a diduction motion transmitted by the model reproducing the upper maxillary. The propulsion motion is reproduced as well by forward motion of the upper model through relatively complicated mechanisms.

SUMMARY OF THE INVENTION

The occlusion simulator according to this invention is designed to overcome these drawbacks as it allows the various mandible motions to be reproduced simply and fully and the models, reproducing the mouth of the patient, are made integral with the occlusion system by screws integral with its branches.

This occlusion simulator mainly consists of two forks, representing the maxillary and the mandible respectively, connected via the fork-holder to each end of a small articulation rod.

The upper fork-holder is connected to the small rod via a longitudinal articulation pin, whereas the lower fork-holder is connected to it by a ball-joint with limited excursion.

The lower fork-holder includes two stacked rectangular parts, each of which includes a hemispherical recess on its contact surface, located opposite one another to form a spherical cavity which accommodates the ball-joint of the articulation small rod, after passage of its stem through a cylindrical opening in the upper part of the lower fork-holder, in the axis of the hemispherical recess in the rear face of this part. The stem of the small rod is undercut over a certain length above the ball-joint to a diameter determined according to the maximum permissible excursion of the lower fork-holder with respect to the small rod.

The lower fork-holder is continuously loaded, in the longitudinal plane of symmetry of the assembly, by two side plates assembled on either side of the upper fork-holder and pistons carried by the lower fork-holder, loaded by springs against a spot facing on the inside surface of the guide plates on the lower part of them.

In a preferential embodiment, the piston return springs are helicoidal springs, one of whose ends is housed in a blind hole drilled in the side of the lower fork-holder and whose other end is supported behind the collar forming the piston head. The piston rods are slightly longer than the width of the clearance on either side of the lower fork-holder, between the fork-holder and the guide plates, to allow the piston heads to be maintained in contact with the spot facing in the side plates, whatever the lateral angle of inclination of the lower fork-holder.

The spacing of the two stacked parts forming the lower fork-holder is adjustable by springs tending to keep the two parts separated and knurled screws limiting the excursion of the springs, which are mounted in blind holes drilled opposite each of the contact faces of the stacked parts forming the lower fork-holder.

The longitudinal excursion of the lower fork-holder with respect to the upper fork-holder is limited at the rear by the heel of the lower fork and the front edge of the side plate flasks, and at the front by stopping of the pistons against the edge of the spot facing against which bear the transverse return pistons of the lower fork-holder.

The upper fork is temporarily assembled with the corresponding fork-holder by a snap-lock system consisting of two grooves pins integral with the fork, two cylindrical cavities drilled in the front face of the fork-holder and two spring-loaded balls, each mounted in a duct located perpendicular to the cylindrical cavities in the plane corresponding to the position of the pin grooves.

The lower fork is assembled by screws to the upper part of the lower fork-holder via a heel, but could easily be attached to the lower fork-holder by a snap-lock system similar to that used to attach the upper fork to its fork-holder.

The models reproducing the patient's mouth are temporarily installed on the forks by knurled setscrews.

The advantages procured by this invention mainly consist of the fact that the occlusion simulator concerned allows the mandible motions to be reproduced by a simple system, i.e.: opening and closing, diduction and propulsion. The snap-lock system attaching the forks to the fork-holders allows a wide range of forks to be combined with a single simulator. This occlusion simulator allows the projection of all prostheses which do not require the use of a facial arc; the capacity of the unit depends on its size.

Other characteristics and advantages will appear in the following description of an occlusion simulator which is an embodiment of the invention, given as a nonrestrictive example with regard to the attached drawings, on which:

DETAILED DESCRIPTION OF THE INVENTION

Figure 1:
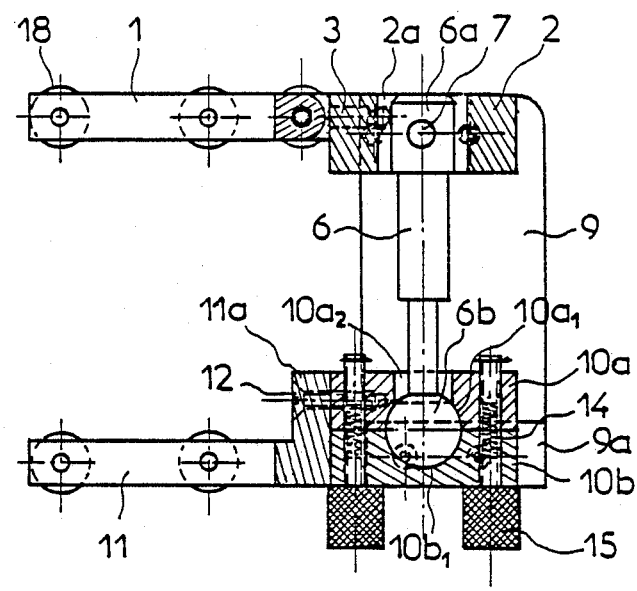
FIG. 1 shows a longitudinal sectional view of the simulator assembly.
Figure 2:
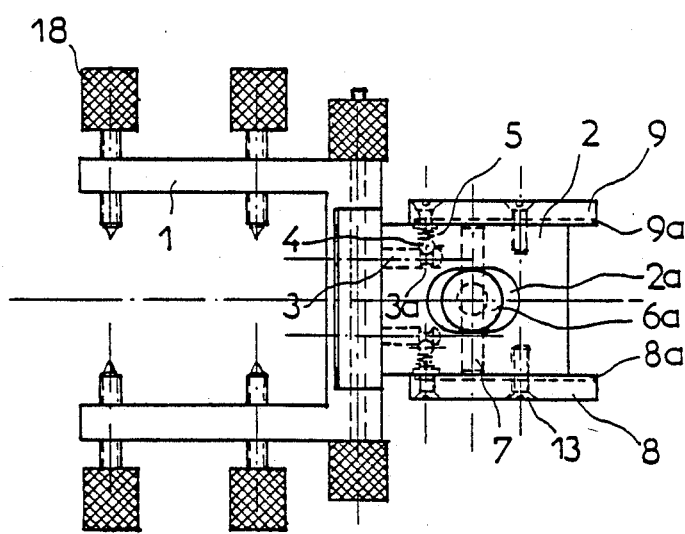
FIG. 2 shows an overhead view of the simulator.
Figure 3:
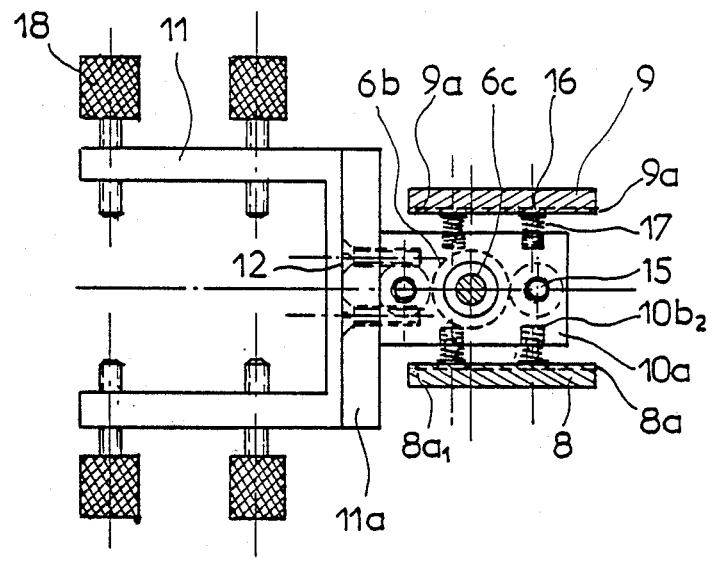
FIG. 3 shows an overhead cross-sectional view of the simulator.
Figure 4:
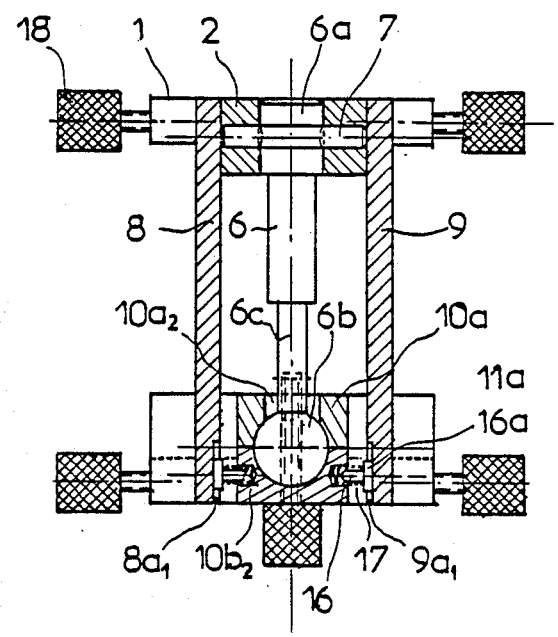
FIG. 4 shows a rear cross-sectional view in the axis of the simulator small rod.

The figures show an occlusion simulator for dental prostheses reproducing mandible motions, mainly including upper fork 1, connected to upper fork-holder 2 by two pins 3a, balls 4 and springs 5; small rod 6 connected to upper fork-holder 2 by pin 7 held in place by side plates 8 and 9 limiting the lateral excursion of lower fork-holder 10 and to lower fork-holder 10 via ball-joint 6b mounted in a spherical cavity consisting of hemispheres 10a, and 10b$_1$ made in the two ports 10a and 10b forming a lower fork-holder 10. Examining FIGS. 1 to 4 more particularly, it can be seen that upper articulated fork 1 is temporarily attached to the forward part of upper fork-holder 2 via two pins 3 with grooves 3a in which are inserted balls 4 loaded by springs 5, whereas lower fork 11 is attached to the front of upper part 10a of lower fork-holder 10 via heel 11a and screw 12. Upper fork-holder 2 is connected to small rod 6 whose upper end 6a is held in an oblong opening 2a located in the plane of symmetry of said upper fork-holder 2 via pin 7 held in its housing by side plates 8 and 9 mounted on the sides of upper fork-holder 2 by screws 13. Lower fork-holder 10 is connected to ball-joint 6b of small rod 6 by two parts, 10a and 10b, respectively including hemispherical recesses $10a_1$ and $10b_1$ in their contact faces which, after assembly, form a spherical cavity enclosing ball-joint 6b after passage of the stem of small rod 6 through cylindrical opening $10a_2$ drilled in lower part 10a, in the axis of hemispherical recess $10a_1$. Springs 14 tending to separate parts 10a and 10b of the lower fork-holder are mounted in blind holes drilled opposite one another in each of the contact faces of said parts 10a and 10b. The excursion of these springs is limited by knurled screws 15 which adjust the value of spacing X between parts 10a and 10b forming lower fork-holder 10. Rod 6 includes undercut part 6c with a diameter determined according to the maximum selected angular excursion. Lower fork-holder 10 is continuously loaded in the plane of symmetry of the assembly by piston 16 connected to lower part 10b of lower fork-holder 17 via helicoidal spring 17 one of whose ends is inserted in blind hole $10b_2$ drilled in lower part 10b and whose other end bears against collar 16a forming the head of pistons 16 to keep the pistons in contact with the surface of spot facings 8a and 9a made on the internal surfaces of side plates 8 and 9, at the lower part of said side plates. The length of the small rod of pistons 16 is determined to allow misalignment of the pistons with respect to the center line of blind holes $10b_2$ housing spring 17 compatible with the maximum permissible angular excursion of lower fork-holder 10.

Figure 5:
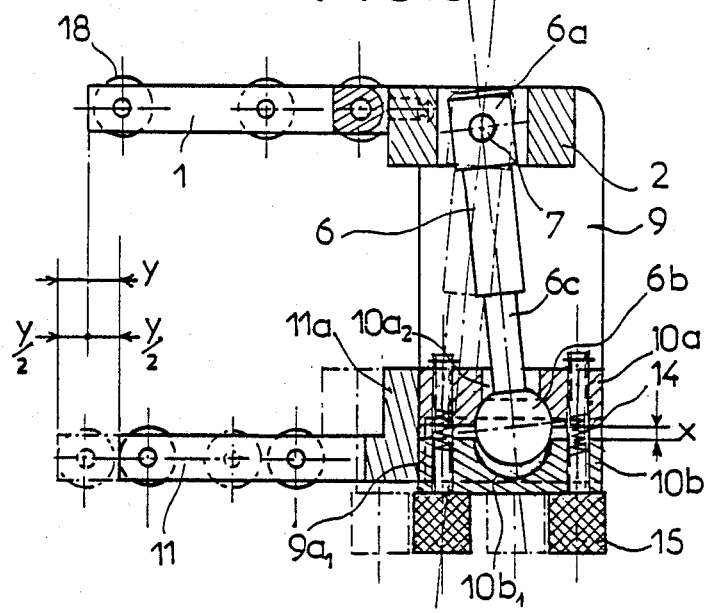
FIG. 5 shows a longitudinal sectional view of the simulator on which the lower fork-holder is against the rear stop, indicating by a dotted-dashed line the position corresponding to the maximum forward excursion.
Figure 6:
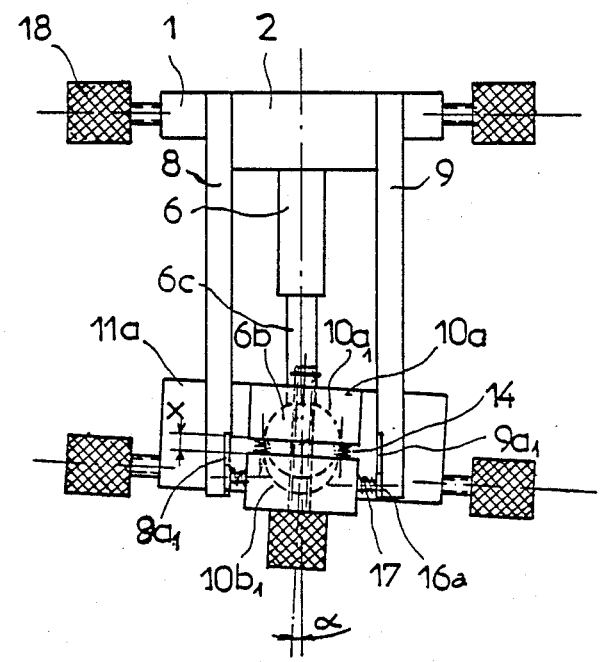
FIG. 6 shows a rear view of the occlusion simulator on which the lower fork-holder is laterally inclined by an angle with a vertical excursion freedom X.

Examining FIGS. 5 and 6, it can be seen that this occlusion simulator allows the combination of the articulation motions of the two fork-holders with diduction and propulsion motions via articulation pin 7, ball-joint 6b and screw 15. The amplitude of these motions is limited at the rear by heel 11a of lower fork 11 and at the front by stopping of the front pistons against front edges $8a_1$ and $9a_1$ of the spots facing made in the internal surface of the side plates; the angle of inclination is limited by the upper edge of cylindrical hole $10a_2$ drilled in upper part 10a of lower fork-holder 10.

By introducing a clearance X between upper part 10a and lower part 10b of the fork-holder, the action on screws 15 allows a change of angle to be obtained to adapt to the case threated, providing a vertical excursion of said lower fork-holder 10 with respect to upper fork-holder 2. The amplitude Y of the longitudinal excursion is distributed equally by a value Y/Z with respect to the position of coincidence of the two forks. The models are attached to the forks by setscrews 18.

I claim:

1. Occlusion simulator for dental prostheses for reproducing mandible motions, comprising upper and lower articulated forks, representing the maxillary and mandible respectively, connected by a small rod, said upper articulated fork representing the maxillary being connected to one end of the small rod by a first fork-holder and an articulation pin, said lower fork representing the mandible being connected to the other end of the small rod by means of a second fork-holder and a ball joint wherein the excursion of the second lower fork-holder with respect to the ball-joint of the small rod is limited longitudinally and transversely by two side plates mounted on either side of said first upper fork-holder.

2. Occlusion simulator as in claim 1, wherein forks are temporarily attached to fork-holders by a snap-lock, via two grooved pins integral with the forks, two cylindrical cavities drilled in the front face of fork-holders and two balls loaded by springs, each mounted in a duct located perpendicular to the cylindrical cavities in the plane corresponding to the position of grooves of said pins.

3. Occlusion simulator as in claim 1, wherein the articulation pin of the upper fork-holder, with respect to small rod is mounted in an opening located transversely to an oblong opening located in the longitudinal plane of symmetry of the fork-holder into which penetrates the upper end of the small rod.

4. Occlusion simulator as in claims 1 or 3, wherein the articulation pin of the upper fork-holder with respect to the small rod is held in place by side plates attached to each side of the first upper fork-holder.

5. Occlusion simulator as in claim 1, wherein the lower fork-holder consists of two stacked rectangular parts each including in its contact face a hemispherical recess located opposite one another to form a spherical cavity housing the ball-joint located at the lower end of the articulation small rod after inserting this small rod through a cylindrical opening with a diameter greater than that of the stem of the small rod, drilled in the upper part of the lower fork-holder in the center line of the hemispherical recess provided in its rear surface.

6. Occlusion simulator as in claim 5, wherein the stem of the small rod is undercut over a certain length above the ball-joint to allow a lateral excursion of the lower fork-holder with respect to the small rod.

7. Occlusion simulator as in claim 1 or 5, wherein the separation between the two stacked parts forming the lower fork-holder is adjustable by springs whose excursion is controlled by knurled screws.

8. Occlusion simulator as in claim 7, wherein springs are mounted in blind holes drilled opposite one another in each of the contact faces of the stacked parts forming the lower fork-holder.

9. Occlusion simulator as in claim 1, wherein the lower fork-holder is continuously loaded in the longitudinal plane of symmetry of the upper fork-holder by pistons supported by the lower fork-holder loaded by springs against spot facings made in the internal surface of guide plates.

10. Occlusion simulator as in claim 9, wherein springs loading pistons are helicoidal springs one of whose ends is housed in a blind hole made in the side of the lower fork-holder and whose other end is supported behind a collar forming the head of pistons.

11. Occlusion simulator is in claim 9 or 10, wherein the length of the rod of pistons is slightly longer than the width of the space existing between the lower fork-holder and each of end plates.

12. Occlusion simulator as in claim 1 or 9, wherein the longitudinal excursion of the lower fork-holder with respect to the upper fork-holder is limited at the rear by the heel of the lower fork and the front edge of plates and at the front by the edges of the spot facings against which bear the heads of pistons transversely loading the lower fork-holder.

13. Occlusion simulator as in claim 1, wherein the models reproducing the patient's mouth are temporarily mounted on forks by knurled setscrews.

* * * * *